United States Patent [19]

Varma

[11] 4,094,840
[45] June 13, 1978

[54] 17-ALKYLTHIO (AND ARYLTHIO) ANDROSTENO[16α,17α-b]BENZODIOXIN-3-ONES

[75] Inventor: Ravi K. Varma, Belle Mead, N.J.

[73] Assignee: E. R. Squibb & Sons, Inc., Princeton, N.J.

[21] Appl. No.: 796,293

[22] Filed: May 12, 1977

[51] Int. Cl.$^2$ ............................................. C07J 73/00
[52] U.S. Cl. ........................................... 260/239.55 R
[58] Field of Search ............................... 260/239.55 R

[56] References Cited

U.S. PATENT DOCUMENTS

| | | | |
|---|---|---|---|
| 3,971,772 | 7/1976 | Cemarusti et al. | 260/239.55 R |
| 3,971,773 | 7/1976 | Cemarusti et al. | 260/239.55 R |

Primary Examiner—Elbert L. Roberts
Attorney, Agent, or Firm—Lawrence S. Levinson; Merle J. Smith; Donald J. Barrack

[57] ABSTRACT

Steroids having the formula

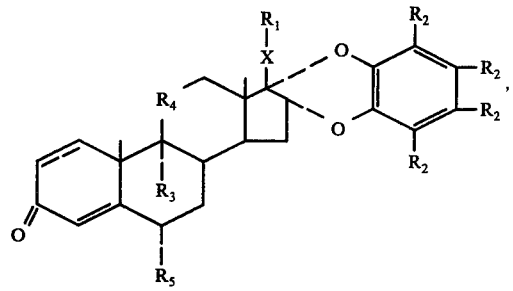

wherein X is —S—,

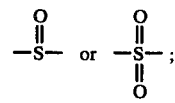

$R_1$ is alkyl, aryl, or acyloxyalkyl; the $R_2$ groups are halogen; $R_3$ is hydrogen or halogen; $R_4$ is carbonyl, β-hydroxymethylene or β-acyloxymethylene; and $R_5$ is hydrogen or fluoro; can be used as antiinflammatory agents.

22 Claims, No Drawings

17-ALKYLTHIO (AND ARYLTHIO) ANDROSTENO[16α,17α-b]BENZODIOXIN-3-ONES

SUMMARY OF THE INVENTION

Steroids having the formula

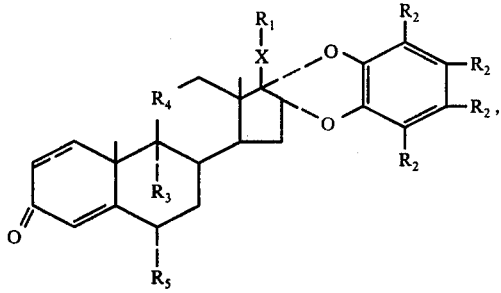

can be used as antiinflammatory agents. In formula I, and throughout the specification, the symbols are as defined below.

X is —S—,

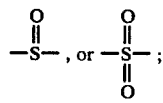

$R_1$ is alkyl, aryl or acyloxyalkyl;

$R_2$ is fluoro, chloro, bromo or iodo (all $R_2$ groups are the same);

$R_3$ is hydrogen, fluoro, chloro, bromo or iodo;

$R_4$ is carbonyl, β-hydroxymethylene or β-acyloxymethylene; and $R_5$ is hydrogen or fluorine. A dotted line in the 1,2 position of a structural formula in this disclosure indicates the optional presence of ethylenic unsaturation.

The term "aryl", as used throughout the specification, refers to phenyl or phenyl substituted with one or two alkyl, alkoxy, or halo groups.

The term "halo", as used throughout the specification, refers to fluoro, chloro, bromo or iodo.

The terms "alkyl" and "alkoxy", as used throughout the specification, refer to groups having 1 to 10 carbon atoms.

The term "acyloxy", as used throughout the specification, whether by itself or as part of a larger group, refers to a group having the formula

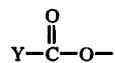

wherein Y is alkyl or aryl.

DETAILED DESCRIPTION OF THE INVENTION

The steroids of this invention can be prepared utilizing as starting materials androstenes having the formula

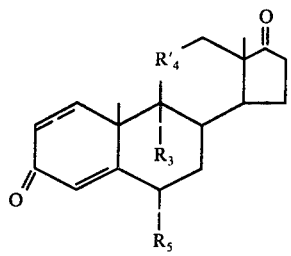

In formula II, and throughout the specification, $R'_4$ is carbonyl or β-hydroxymethylene.

Reaction of an androstene of formula II with a thiol compound having the formula $$R'_1\text{—SH} \qquad \qquad \text{III}$$

in the presence of a Lewis acid (e.g., boron trifluoride etherate), yields an intermediate having the formula

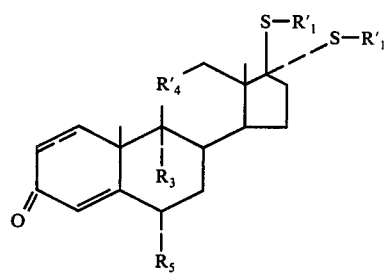

In formulas III and IV, and throughout the specification, $R'_1$ is alkyl or aryl. The reaction can be run in an organic solvent (e.g., a halogenated hydrocarbon), or mixture of organic solvents. The use of some glacial acetic acid improves yields. Reaction conditions are not critical, and the reaction can be conveniently run at room temperature, preferably in an inert atmosphere (e.g., argon or nitrogen). Better yields may be obtained with relatively short reaction times (less than 1 hour).

An androstene of formula IV can be converted to the corresponding steroid having the formula

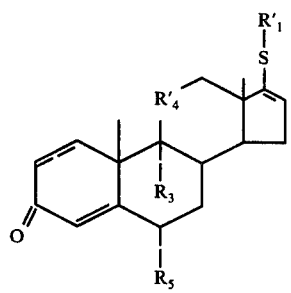

by simply heating the steroid in an inert solvent (e.g., diethylbenzene or dichlorobenzene).

The steroid products of formula I wherein $R_1$ is alkyl or aryl, $R_4$ is carbonyl or β-hydroxymethylene and X is divalent sulfur can be obtained by reacting a steroid of formula V with an o-benzoquinone having the formula

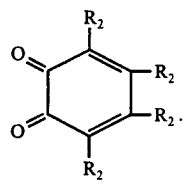

VI

The reaction proceeds at room temperature, yielding a product having the formula

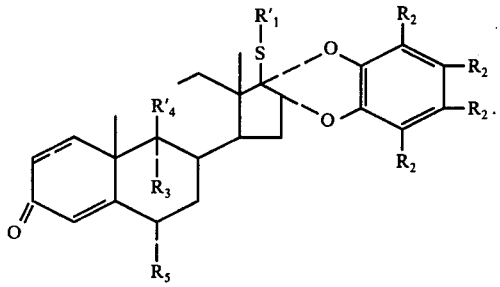

VII

Oxidation of an androstene of formula VII with a peracid (e.g., m-chloroperbenzoic acid), a peracid salt (e.g., sodium m-periodate) or a peroxide (e.g., hydrogen peroxide) yields the corresponding sulfinyl product having the formula

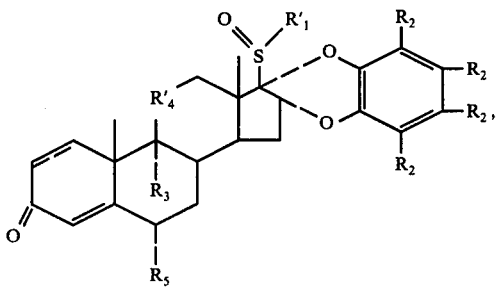

VIII or the corresponding sulfonyl product having the formula

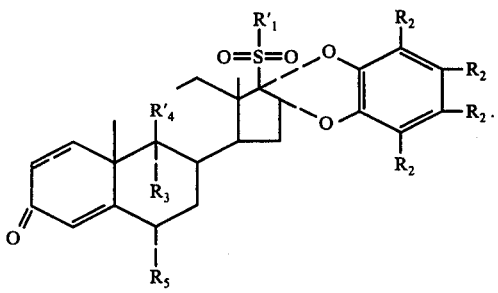

IX

The use of one equivalent of oxidizing agent will yield predominantly the sulfinyl derivative of formula VIII and the use of two or more equivalents of oxidizing agent will yield predominantly the sulfonyl derivative of formula IX. Meta-chloroperbenzoic acid is the preferred oxidizing agent. The oxidation reaction can be run in an organic solvent, e.g., a halogenated hydrocarbon such as chloroform.

Those steroids of formula I wherein $R_1$ is acyloxyalkyl are prepared by first oxidizing a steroid of formula V, wherein $R'_1$ is alkyl, using one equivalent of oxidizing agent, to obtain a steroid having the formula

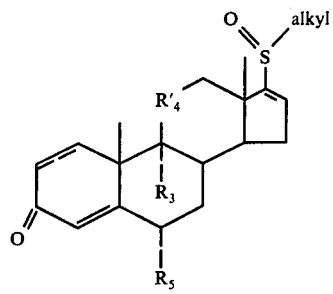

X

A 17-alkylsulfinyl steroid of formula X can be reacted with an appropriate acid anhydride, and a basic catalyst such as the sodium salt of the corresponding acid, to yield the corresponding 17-[[(acyloxy)alkyl]thio]steroid having the formula

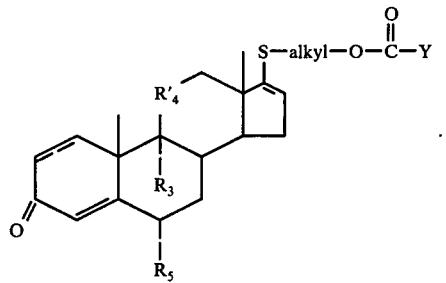

XI

Reaction of a steroid of formula XI with an o-benzoquinone of formula VI yields a product of formula I wherein $R_1$ is acyloxyalkyl and X is divalent sulfur. These steroids can be oxidized as described above to yield the corresponding steroids of formula I wherein X is

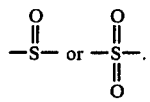

The 11β-acyloxy derivatives of formula I can be obtained by acylating the corresponding 11β-hydroxy steroid of formula I, by acylating the corresponding 11β-hydroxy steroid of formula II and proceeding as described above, or by acylating a corresponding 11β-hydroxy steroid intermediate and proceeding as described above.

Many alternative processes for preparing the steroids of formula I will be readily apparent to a person of ordinary skill in the art. For example, any of the 17-sulfonyl products can be obtained by oxidizing the corresponding 17-sulfinyl steroids of formula I.

The oxidation of a 17-thio product to yield a 17-sulfinyl steroid of formula I results in a mixture of two isomers, which may be separated using conventional techniques.

The steroids of formula I can be used in lieu of known glucocorticoids in the treatment of inflammatory conditions; e.g., rheumatoid arthritis. They can be administered in the same manner as hydrocortisone, the dosage being adjusted for the relative potency of the particular steroid. Additionally, the steroids of this invention can be used topically in lieu of known glucocorticoids in the treatment of skin conditions such as dermatitis, psoriasis, sunburn, neurodermatitis, eczema or anogenital pruritus.

When given orally, the steroids of this invention may be used in a dosage range of 0.1 to 200 milligrams, preferably 0.3 to 100 milligrams, for a 70 kg. mammal. If administered topically, the steroids of this invention may be used in the range of 0.01 to 5.0% by weight, preferably 0.05 to 2.0% by weight, in a conventional cream, ointment, lotion or the like.

The following examples are specific embodiments of this invention.

EXAMPLE 1

5′,6′,7′,8′-Tetrachloro-9-fluoro-2′,3′-dihydro-11β-hydroxy-17-(methylthio)androsta-1,4-dieno[16α,17α-b][1,4]benzodioxin-3-one (A)

9-Fluoro-11β-hydroxy-17,17-bis(methylthio)androsta-1,4-dien-3-one

A solution of 9-fluoro-11β-hydroxyandrosta-1,4-diene-3,17-dione (2.0 g) in glacial acetic acid (25 ml) is mixed at room temperature with a solution of methanethiol (2.4 g) in dichloromethane (16 ml) and boron trifluoride etherate (0.5 ml). After 1.5 hours, the mixture is poured into water and diluted with chloroform. The organic layer is then separated, washed with a dilute sodium bicarbonate solution and water, dried and evaporated in vacuo. The residue is absorbed on a column of silica gel (50 g). Elution of the column with chloroform removed the non-steroidal impurities and a product resulting from thiol addition to $\Delta^1$. Subsequent elution with chloroform affords the desired material as a solid (957 mg). Finally, elution with chloroform-ethyl acetate (95:5) affords the unreacted steroid (345 mg). A specimen of the 957 mg solid is crystallized once from chloroform-methanol to afford the analytical sample of the title compound, melting point 305° C (dec.).

Anal. Calc'd. for $C_{21}H_{29}FO_2S_2$: C, 63.40; H, 7.37; F, 4.79; S, 16.17. Found: C, 63.48; H, 7.21; F, 4.95; S, 16.21.

(B)

9-Fluoro-11β-hydroxy-17-(methylthio)androsta-1,4,16-trien-3-one

A suspension of 9-fluoro-11β-hydroxy-17,17-bis(methylthio)androsta-1,4-diene-3-one (3.6 g) in diethylbenzene (250 ml) is slowly distilled from a bath at 220° C. In a few minutes, a clear solution results and the starting material disappears. On cooling in an ice bath, the solution deposits small needles of the analytical specimen of the title compound, (2.9 g), melting point 268° C (dec.). (discoloration starts at 263° C).

Anal. Calc'd. for $C_{20}H_{25}FO_2S$: C, 68.93; H, 7.23; F, 5.00; S, 9.20. Found: C, 68.68; H, 7.20; F, 4.92; S, 9.09.

(C)

5′,6′,7′,8′-Tetrachloro-9-fluoro-2′,3′-dihydro-11β-hydroxy-17-(methylthio)androsta-1,4-dieno[16α,17α-b][1,4]benzodioxin-3-one A suspension of 523 mg of 9-fluoro-11β-hydroxy-17-(methylthio)androsta-1,4,16-trien-3-one in 100 ml of dry tetrahydrofuran is gently warmed on a steam bath until a homogeneous solution is obtained. The solution is cooled to room temperature and 369 mg of tetrachloro-o-benzoquinone is added. After about 16 hours stirring the solution is evaporated in vacuo to give a foam. This is rinsed with 1:1 chloroform-ethyl acetate, and the insoluble material is filtered and recrystallized from chloroform-methanol to give 460 mg of the title compound, melting point 301°-302° C.

Anal. Calc'd. for $C_{26}H_{25}Cl_4FO_4S$: C, 52.54; H, 4.24; Cl, 23.86; F, 3.20; S, 5.40. Found: C, 52.75; H, 4.21; Cl, 23.64; F, 3.48; S, 5.68.

EXAMPLE 2

5′,6′,7′,8′-Tetrachloro-9-fluoro-2′,3′-dihydro-11β-hydroxy-17-(methylsulfinyl)androsta-1,4-dieno[16α1-7α-b][1,4]benzodioxin-3-one A suspension of 380 mg of 5′,6′,7′,8-tetrachloro-9-fluoro-2′,3′-dihydro-11β-hydroxy-17-(methylthio)androsta-1,4-dieno[16α,17α-b][1,4]benzodioxin-3-one in 400 ml of chloroform is gently warmed on a steam bath until a homogeneous solution is obtained. After cooling to room temperature, a solution of 130 mg of m-chloroperbenzoic acid (~85%) in 40 ml of chloroform is added in the course of 15 minutes. The resulting solution is stirred for 40 minutes, washed with a diluted sodium bicarbonate solution and water, dried over anhydrous sodium sulfate and evaporated in vacuo to give 440 mg of a foam. This is redissolved in chloroform and chromatographed on pre-coated silica gel TLC (thin layer chromatography) plates (2 × 200 × 200 mm, 3:97 methanol-chloroform development) to give two isomers: isomer A (230 mg) and isomer B (115 mg). Isomer A is crystallized from chloroform-methanol to give 170 mg of tlc-homogeneous title compound, melting point 288°-289° C (dec.) with consistent spectral data. Isomer B is crystallized from chloroform-methanol to give 100 mg of the title compound, melting point 284°-285° C (dec.).

EXAMPLE 3

5′,6′,7′,8′-Tetrachloro-9-fluoro-2′,3′-dihydro-11β-hydroxy-17-(methylsulfonyl)androsta-1,4-dieno[16α,-17α-b][1,4]benzodioxin-3-one A solution of 375 mg of 5′,6′,7′,8′-tetrachloro-9-fluoro-2′,3′-dihydro-11β-hydroxy-17-(methylsulfinyl)androsta-1,4-dieno[16α,17α-b][1,4]benzodioxin-3-one (isomer A, see Example 2) in 300 ml of dichloromethane is stirred with 137 mg of m-chloroperbenzoic acid (85%) at room temperature for about 16 hours. The solution is washed with a saturated sodium bicarbonate solution, water, dried over anhydrous sodium sulfate and filtered. The filtrate is passed through a 20 g silica gel column and eluted with chloroform. The solvent is evaporated in vacuo to give the tlc-homogeneous title compound (400 mg). One crystallization from chloroform-methanol gives 310 mg of the title compound, melting point 348°-350° C, with consistent spectral data.

Anal. Calc'd. for $C_{26}H_{25}Cl_4FO_6S$: C, 49.85; H, 4.02; Cl, 22.64; F, 3.03; S, 5.12. Found: C, 50.10; H, 3.91; Cl, 22.79; F, 3.30; S, 5.03.

EXAMPLE 4

5′,6′,7′,8′-Tetrachloro-17-(ethylthio)-9-fluoro-2′,3′-dihydro-11β-hydroxyandrosta-1,4-dieno[16α,17α-b][1,4]benzodioxin-3-one (A)

17,17-Bis(ethylthio)-9-fluoro-11β-hydroxyandrosta-1,4-dien-3-one

A solution of 9.5 g of 9-fluoro-11β-hydroxyandrosta-1,4-diene-3,17-dione in 50 ml of dichloromethane and 50 ml of glacial acetic acid is stirred with 11.2 g of ethanethiol and 7.5 ml of boron trifluoride etherate at room temperature under nitrogen. After 1.5 hours the solution is diluted with 350 ml of chloroform. The chloroform solution is washed with water, saturated sodium bicarbonate solution and water, dried over anhydrous sodium sulfate and evaporated in vacuo to give 11 g of a foam. This is dissolved in hexane-chloroform (2:1) and chromatographed on a 200 g-silica gel column. Elution with hexane-chloroform (2:1 and 1:1) gives 2.1 g of a tlc-homogeneous material. Crystallization from acetone-hexane gives 1.05 g of the title compound, melting point 276°–277° C (dec.), with consistent spectral data.

Anal. Calc'd. for $C_{23}H_{33}FO_2S_2$: C, 65.05; H, 7.83; F, 4.47; S, 15.10. Found: C, 65.31; H, 7.80; F, 4.71; S, 15.01.

(B)

17-(Ethylthio)-9-fluoro-11β-hydroxyandrosta-1,4,16-trien-3-one

A suspension of 1.8 g of 17,17-bis(ethylthio)-9-fluoro-11β-hydroxyandrosta-1,4-dien-3-one in 120 ml of diethylbenzene is stirred at 190° C (oil bath temperature) for 1 hour. The solution is cooled to 0° C and the solid that precipitates is filtered. This is redissolved in 1:9 hexane-chloroform and chromatographed on a 60 g-silica gel column. Elution with 1:9 hexane-chloroform gives 1.35 g of a tlc-homogeneous material. Crystallization from chloroform-methanol gives 680 mg of the title compound, melting point 282°–283° C (dec.), with consistent spectral data.

Anal. Calc'd. for $C_{21}H_{27}FO_2S$: C, 69.58; H, 7.51; F, 5.24; S, 8.85. Found: C, 69.46; H, 7.32; F, 5.47; S, 8.71.

(C)

5',6',7',8'-Tetrachloro-17-(ethylthio)-9-fluoro-2',3'-dihydro-11β-hydroxyandrosta-1,4-dieno[16α,17α-b][1,4]-benzodioxin-3-one To a solution of 1.35 g of 17-(ethylthio)-9-fluoro-11β-hydroxyandrosta-1,4,16-trien-3-one in 110 ml of dry tetrahydrofuran is added 1.0 g of tetrachloro-o-benzoquinone. The red solution is stirred at room temperature under nitrogen for about 16 hours, and more tetrachloro-o-benzoquinone (180 mg) is added. The solution is stirred at room temperature under nitrogen for 4 hours. Water (2 ml) is added and the solution is evaporated in vacuo. The residue is dissolved in 1:3 hexane-chloroform and chromatographed on a 100 g-silica gel column. Elution with 1:3 hexane-chloroform gives 1.85 g of a tlc-homogeneous material. Crystallization from chloroform-methanol gives 0.9 g of the title compound, melting point 287°–288° C (dec.), with consistent spectral data.

Anal. Calc'd. for $C_{27}H_{27}Cl_4FO_4S$: C, 53.30; H, 4.47; Cl, 23.31; F, 3.12; S, 5.27. Found: C, 53.10; H, 4.38; Cl, 23.47; F, 3.42; S, 5.29.

EXAMPLE 5

5',6',7',8'-Tetrachloro-17-(ethylsulfinyl)-9-fluoro-2',3'-dihydro-11β-hydroxyandrosta-1,4-dieno[16α,17α-b][1,4]-benzodioxin-3-one A suspension of 1.5 g of 5',6',7',8'-tetrachloro-17-(ethylthio)-9-fluoro-2',3'-dihydro-11β-hydroxyandrosta-1,4-dieno[16α,17α-b][1,4]benzodioxin-3-one (see Example 4) in 550 ml of chloroform is gently warmed on a steam bath until a homogeneous solution is obtained. After cooling to room temperature, a solution of 549 mg of m-chloroperbenzoic acid (85%) in 30 ml of chloroform is added in the course of 5 minutes. The resulting solution is stirred for 1.5 hours at room temperature under nitrogen, washed with a saturated sodium bicarbonate solution and water, dried over anhydrous sodium sulfate and evaporated in vacuo to give 1.35 g of a foam. This is dissolved in chloroform and chromatographed on precoated silica gel TLC plates (2 × 200 × 200 mm, 1:4 ethyl-acetate-chloroform development) to give two isomers; isomer A (600 mg) and isomer B (298 mg). Isomer A is crystallized from methanol-chloroform to give 420 mg of tlc-homogeneous title compound, melting point 252°–253° C, with consistent spectral data. Isomer B on similar crystallization affords 260 mg of the title compound, melting point 217°–218° C.

EXAMPLE 6

5',6',7',8'-Tetrachloro-17-(ethylsulfonyl)-9-fluoro-2',3'-dihydro-11β-hydroxyandrosta-1,4-dieno[16α,17α-b][1,4]-benzodioxin-3-one A solution of 350 mg of 5',6',7',8'-tetrachloro-17-(ethylsulfinyl)-9-fluoro-2',3'-dihydro-11β-hydroxyandrosta-1,4-dieno[16α,17α-b][1,4]-benzodioxin-3-one (isomer A, see Example 5) in 200 ml of chloroform is stirred with 125 mg of m-chloroperbenzoic acid (85%) at room temperature for about 16 hours. The resulting solution is washed with 5% sodium carbonate solution and water, dried over anhydrous sodium sulfate and evaporated in vacuo to give 360 mg of solid. This is dissolved in chloroform and chromatographed on a 25 g-silica gel column. Elution with chloroform gives 320 mg of a tlc-homogeneous material. Crystallization from chloroform-methanol gives 260 mg of the title compound, melting point 342°–343° C (dec.), with consistent spectral data.

Anal. Calc'd. for $C_{27}H_{27}Cl_4FO_6S$: C, 50.64; H, 4.25; Cl, 22.15; F, 2.97; S, 5.01. Found: C, 50.51; H, 4.07; Cl, 22.40; F, 3.55; S, 4.95.

EXAMPLE 7

5',6',7',8'-Tetrachloro-9-fluoro-2',3'-dihydro-11β-hydroxy-17-(phenylthio)androsta-1,4-dieno[16α,17α-b][1,4]benzodioxin-3-one (A)

9-Fluoro-11β-hydroxy-17,17-bis(phenylthio)-androsta-1,4-dien-3-one

A solution of 9.0 g of 9-fluoro-11β-hydroxyandrosta-1,4-diene-3,17-dione in 50 ml of dichloromethane and 50 ml of glacial acetic acid is stirred with 18.68 g of thiophenol and 7.5 ml of boron trifluoride ethereate at room temperature under nitrogen. After 50 minutes the solution is diluted with 350 ml of chloroform. The chloroform solution is washed successively with water, saturated sodium bicarbonate solution and water, dried over anhydrous sodium sulfate and evaporated in vacuo to give 11.6 g of an oil. This is dissolved in 1:3 hexane-chloroform and chromatographed on a 200 g-silica gel column. Elution with 1:3 hexane-chloroform and chloroform gives 3.5 of a tlc-homogeneous material. Crystallization from chloroform-methanol gives 2.0 g of the title compound, melting point 249°–250° C (dec.), with consistent spectral data.

Anal. Calc'd. for $C_{31}H_{33}FO_2S_2$: C, 71.50; H, 6.39; F, 3.65; S, 12.32. Found: C, 71.66; H, 6.49; F, 3.92; S, 12.41.

(B)

9-Fluoro-11β-hydroxy-17-(phenylthio)androsta-1,4,16-trien-3-one

A suspension of 3.0 g of 9-fluoro-11β-hydroxy-17,17-bis(phenylthio)androsta-1,4-dien-3-one in 150 ml of diethylbenzene is stirred at 190° C for 45 minutes. The solution is cooled at 0° C and a solid crystallizes. This is filtered and dried in vacuo to give 2.3 g of material. Recrystallization from chloroform-methanol gives 1.1 g of the title compound, melting point 250°–251° C (dec.), with consistent spectral data.

Anal. Calc'd. for $C_{25}H_{27}FO_2S$: C, 73.14; H, 6.63; F, 4.63; S, 7.81. Found: C, 73.28; H, 6.74; F, 4.52; S, 7.84.

(C)

5′,6′,7′,8′-Tetrachloro-9-fluoro-2′,3′-dihydro-11β-hydroxy-17-(phenylthio)androsta-1,4-dieno[16α,17α-b][1,4]benzodioxin-3-one To a solution of 1.8 g of 9-fluoro-11β-hydroxy-17-(phenylthio)androsta-1,4,16-trien-3-one in 200 ml of dry tetrahydrofuran is added 1.19 g of tetrachloro-o-benzoquinone. The red solution is stirred at room temperature under nitrogen for 65 hours (the reaction is completed after 24 hours). Water (2.0 ml) is added and the solution is evaporated in vacuo. The residue is dissolved in 1:2 hexane-chloroform and chromatographed on a 120 g-silica gel column. Elution with hexane-chloroform (1:2 and 1:3) gives 2.5 g of a tlc-homogeneous material. Crystallization from chloroform-methanol gives 1.6 g of the title compound, melting point 279°–280° C (dec.), with consistent spectral data.

Anal. Calc'd. for $C_{31}H_{27}Cl_4FO_4S$: C, 56.72; H, 4.14; Cl, 21.61; F, 2.89; S, 4.88. Found: C, 56.51; H, 4.17; Cl, 21.79; F, 3.10; S, 4.85.

EXAMPLE 8

5′,6′,7′,8′-Tetrachloro-9-fluoro-2′,3′-dihydro-11β-hydroxy-17-(phenylsulfinyl)androsta-1,4-dieno[16α,17α-b][1,4]benzodioxin-3-one To a solution of 2.1 g of 5′,6′,7′,8′-tetrachloro-9-fluoro-2′,3′-dihydro-11β-hydroxy-17-(phenylthio)androsta-1,4-dieno[16α,17α-b][1,4]benzodioxin-3-one (see Example 7) in 500 ml of chloroform is added a solution of 715 mg of m-chloroperbenzoic acid (85%) in the course of 6 minutes. The resulting solution is stirred for 3 hours at room temperature under nitrogen, washed with a saturated sodium bicarbonate solution and water, dried over anhydrous sodium sulfate and evaporated in vacuo to give 2.2 g of a foam. This is dissolved in chloroform-hexane (4:1) and chromatographed on a 120-gram silica gel column. Elution with chloroform-hexane (4:1 and 9:1) and chloroform-ethylacetate (9:1) gives isomer A (1.0 g) and a mixture of isomer A and isomer B (900 mg). [5′,6′,7′,8′-tetrachloro-9-fluoro-2′,3′-dihydro-11β-hydroxy-17-(phenylsulfonyl)androsta-1,4-dieno[16α,17α-b][1,4]benzodioxin-3-one (200 mg) is also isolated from this chromatography]. Isomer A is crystallized from chloroform-hexane to give 650 mg of the tlc-homogeneous title compound, melting point 219°–220° C (dec.), with consistent spectral data. The mixture of Isomer A and Isomer B (900 mg) is further subjected to chromatography over silica gel to isolate isomer B (600 mg) which on recrystallization from chloroform-hexane has a melting point of 215°–217° C (dec.).

EXAMPLE 9

5′,6′,7′,8′-Tetrachloro-9-fluoro-2′,3′-dihydro-11β-hydroxy-17-(phenylsulfonyl)androsta-1,4-dieno[16α,17α-b][1,4]benzodioxin-3-one A solution of 400 mg of 5′,6′,7′,8′-tetrachloro-9-fluoro-2′,3′-dihydro-11β-hydroxy-17-(phenylsulfinyl)androsta-1,4-dieno[16α,17α-b][1,4]benzodioxin-3-one (Isomer A, see Example 8) in 200 ml of chloroform is stirred with 113 mg of m-chloroperbenzoic acid (85%) at room temperature for 4 hours. The resulting solution is washed with a saturated sodium bicarbonate solution and water, dried over anhydrous sodium sulfate and evaporated in vacuo to give a gum (425 mg). This is dissolved in chloroform-hexane (9:1) and chromatographed on a 25 g-silica gel column. Elution with chloroform-hexane (9:1) gives 400 mg of a tlc-homogeneous material. Crystallization from chloroform-methanol gives 310 mg of the title compound, melting point 310°–313° C (dec.) with consistent spectral data.

Anal. Calc'd. for $C_{31}H_{27}Cl_4FO_6S$: C, 54.08; H, 3.95; Cl, 20.60; F, 2.76; S, 4.66. Found: C, 54.03; H, 3.71; Cl, 20.48; F, 3.84; S, 4.89.

EXAMPLE 10

17-[[(Acetyloxy)methyl]thio]-5′,6′,7′,8′-tetrachloro-9-fluoro-2′,3′-dihydro-11β-hydroxyandrosta-1,4-dieno[-16α,17α-b][1,4]-benzodioxin-3-one (A)

9-Fluoro-11β-hydroxy-17-(methylsulfinyl)androsta-1,4,16-trien-3-one

To a stirred solution of 1.0 g of 9-fluoro-11β-hydroxy-17-(methylthio)androsta-1,4,16-trien-3-one (see Example 1B) in chloroform (500 ml) is added a solution of 85% m-chloroperbenzoic acid (552 mg) in chloroform (10 ml) in the course of 3.0 minutes. In less than 10 minutes, the peracid and the starting steroid disappear. The solution is then washed with a dilute potassium carbonate solution and water, dried, concentrated (to about 10 ml) and diluted with ethyl acetate resulting in the precipitation of small, light needles of the analytical specimen of the title compound, (1.0 g), melting point 268°–269° C (dec.). This is a mixture of the two sulfinyl isomers.

Anal. Calc'd. for $C_{20}H_{25}FO_3S$: C, 65.90; H, 6.90; F, 5.00; S, 8.80. Found: C, 65.76; H, 6.98; F, 4.92; S, 9.09.

(B)

17-[[(Acetyloxy)methyl]thio]-9-fluoro-11β-hydroxyandrosta-1,4,16-trien-3-one

A mixture of 1.5 g of 9-fluoro-11β-hydroxy-17-(methylsulfinyl)androsta-1,4,16-trien-3-one, 70 ml of acetic anhydride and 2 g of fused sodium acetate is heated at 110° C under nitrogen for 2 hours. The acetic anhydride is partially removed by distillation under vacuum and the resulting slurry is diluted with 1:1 chloroform-water. The organic layer is separated, washed with diluted sodium bicarbonate solution, water, dried over anhydrous sodium sulfate and evaporated in vacuo. The residue is dissolved in 4:1 chloroform-hexane and chromatographed on a 40 g-silica gel column. Elution with 1:4 hexane-chloroform gives 940 mg of slightly impure material. Two crystallizations from acetone-hexane give 350 mg of the title compound, melting point 193°–194° C, with consistent spectral data.

Anal. Calc'd. for $C_{22}H_{27}FO_4S$: C, 65.00; H, 6.70; F, 4.67; S, 7.89. Found: C, 64.75; H, 6.73; F, 4.39; S, 8.15.

(C)

17-[[(Acetyloxy)methyl]thio]-5',6',7',8'-tetrachloro-9-fluoro-2',3'-dihydro-11β-hydroxyandrosta-1,4-dieno-[16α,17α-b][1,4]benzodioxin-3-one To a solution of 406 mg of 17-[[(acetyloxy)methyl]-thio]-9-fluoro-11β-hydroxyandrosta-1,4,16-triene-3-one in 50 ml of dry tetrahydrofuran is added 246 mg of tetrachloro-o-benzoquinone. The red solution is stirred under nitrogen at room temperature for about 16 hours. More of the tetrachloro-o-benzoquinone (246 mg) is added two more times after every 20 hours until the starting material disappears (tlc). Water (10 drops) is added to the dark red solution and stirred for another 1 hour. The solvent is evaporated in vacuo and the residue is dissolved in chloroform and passed through a 15 g-silica gel column. Elution with chloroform gives 600 mg of slightly impure product. Two crystallizations from chloroform-methanol give 310 mg of the title compound, melting point 298°–299° C (dec.) with consistent spectral data.

Anal. Calc'd. for $C_{28}H_{27}Cl_4FO_6S$: C, 51.55; H, 4.17; Cl, 21.74; F, 2.91; S, 4.92. Found: C, 51.25; H, 4.31; Cl, 21.53; F, 3.17; S, 5.00.

EXAMPLE 11

17-[[(Acetyloxy)methyl]sulfinyl]-5',6',7',8'-tetrachloro-9-fluoro-2',3'-dihydro-11β-hydroxyandrosta-1,4-dieno[-16α,17α-b]-[1,4]benzodioxin-3-one A suspension of 482 mg of 17-[[(acetyloxy)methyl]-thio]-5',6',7',8'-tetrachloro-9-fluoro-2',3'-dihydro-11β-hydroxyandrosta-1,4-dieno[16α,17α-b][1,4]benzodioxin-3-one (see Example 10) in 500 ml of chloroform is gently warmed on a steam bath until a homogeneous solution is obtained. After cooling to room temperature, a solution of 152 mg of m-chloroperbenzoic acid (85%) in 40 ml of chloroform is added in a 15-minute period. The solution is stirred for 1 hour, washed with a diluted sodium bicarbonate solution and water, dried over anhydrous sodium sulfate and evaporated in vacuo to give a foam. This is redissolved in chloroform and chromatographed on precoated silica gel TLC plates (2 × 200 × 200 mm, 3:97 methanol-chloroform development) to give two isomers; isomer A (220 mg) and isomer B (100 mg). Isomer A is crystallized from chloroform-methanol to give 165 mg (33.4%) of the tlc-homogeneous title compound, melting point 289°–290° C (dec.), with consistent spectral data. Isomer B is crystallized in a similar manner to give a product having a melting point 292°–294° C.

EXAMPLE 12

17-[[(Acetyloxy)methyl]sulfonyl]-5',6',7',8'-tetrachloro-9-fluoro-2',3'-dihydro-11β-hydroxyandrosta-1,4-dieno[-16α,17α-b][1,4]benzodioxin-3-one Oxidation of 17-[[(acetyloxy)methyl]sulfinyl]-5',6',7',8'-tetrachloro-9-fluoro-2',3'-dihydro-11β-hydroxyandrosta-1,4-dieno[16α,17α-b][1,4]benzodioxin-3-one (isomer A, Example 11) with 1.1 equivalents of m-chloroperbenzoic acid, following the procedure described in Example 3, yields the title compound, melting point 291°–293° C (dec.).

EXAMPLE 13

11β-(Acetyloxy)-5',6',7',8'-tetrabromo-9-fluoro-2',3'-dihydro-17-(phenylthio)androsta-1,4-dieno[16α,17α-b][1,4]benzodioxin-3-one (A)

11β-(Acetyloxy)-9-fluoroandrosta-1,4-diene-3,17-dione

A solution of 9-fluoro-11β-hydroxyandrosta-1,4-diene-3,17-dione (2.0 g) in a mixture of acetic anhydride (20 ml) and acetic acid (10 ml) containing p-toluenesulfonic acid (200 mg) is kept at room temperature for 40 hours. Sodium acetate (1.0 g) is added and the mixture is evaporated in vacuo. The residue is diluted with water and extracted with chloroform. The chloroform extracts are combined, washed with a dilute sodium bicarbonate solution and water, dried, evaporated and the residue is chromatographed on a column of silica gel to afford the title compound (1.6 g), melting point 229°–230° C.

(B)

11β-(Acetyloxy)-17,17-bis(phenylthio)-9-fluoroandrosta-1,4-diene-3-one

A solution of 11β-(acetyloxy)-9-fluoroandrosta-1,4-diene-3,17-dione (6.8 g) in a mixture of dichloromethane (35 ml) and glacial acetic acid (35 ml) is mixed with borontrifluoride etherate (4.5 g) and the solution is stirred at room temperature for one hour. The mixture is then diluted with chloroform, washed successively with water, a dilute sodium bicarbonate solution and water, dried and evaporated in vacuo. The residue is chromatographed over silica gel to afford the title compound (2.3 g), melting point 180°–184° C.

(C)

11β-(Acetyloxy)-9-fluoro-17-(phenylthio)-androsta-1,4,16-trien-3-one

A solution of 11β-(acetyloxy)-17,17-bis(phenylthio)-9-fluoroandrosta-1,4-diene-3-one (2.3 g) in diethylbenzene (150 ml) is heated in a bath at 190° C for 60 minutes. The solution is then cooled in an ice bath and the separated title compound is isolated by filtration and washed with hexane to afford 2.15 g of the title compound, melting point 229°–231° C.

(D)

11β-(Acetyloxy)-5',6',7',8'-tetrabromo-9-fluoro-2',3'-dihydro-17-(phenylthio)androsta-1,4-dieno[16α,17α-b][1,4]benzodioxin-3-one To a solution of 2.0 g of 11β-(acetyloxy)-9-fluoro-17-(phenylthio)-androsta-1,4,16-trien-3-one in 300 ml of dry tetrahydrofuran is added 2.0 g of tetrabromo-o-benzoquinone. The solution is stirred under nitrogen for 24 hours to yield the title compound.

EXAMPLE 14

17-[[(Benzoyloxy)methyl]thio]-5',6',7',8',9-pentafluoro-2',3'-dihydro-11β-hydroxyandrosta-1,4-dieno[16α,17α-b][1,4]benzodioxin-3-one (A)

17-[[(Benzoyloxy)methyl]thio]-9-fluoro-11β-hydroxyandrosta-1,4,16-trien-3-one

A solution of 9-fluoro-11β-hydroxy-17-(methylthio)androsta-1,4,16-trien-3-one (100 mg, see Example 1B) in 30 ml of xylene containing 4.0 g of benzoic anhydride and 300 mg of sodium methoxide is stirred at 130° C for 48 hours. The product is then isolated and chromatographed over silica gel to yield 80 mg of the title compound, melting point 220°–222° C.

(B)
17-[[(Benzoyloxy)methyl]thio]-5',6',7',8',9-pentafluoro-2',3'-dihydro-11β-hydroxyandrosta-1,4-dieno[16α,17α-b][1,4]benzodioxin-3-one To a solution of 75 mg of 17-[[(benzoyloxy)methyl]-thio]-9-fluoro-11β-hydroxyandrosta-1,4,16-trien-3-one in 50 ml of dry tetrahydrofuran is added 200 mg of tetrafluoro-o-benzoquinone. The solution is stirred under nitrogen for 24 hours to yield the title compound.

EXAMPLES 15–18

Following the procedure of Example 1, but substituting the steroid listed in column I for 9-fluoro-11β-hydroxyandrosta-1,4-diene-3,20-dione, the compound listed in column II for methanethiol and the compound listed in column III for tetrachloro-o-benzoquinone, yields the steroid listed in column IV.

| | Column I | Column II | Column III | Column IV |
|---|---|---|---|---|
| 15 | 11β-hydroxyandrosta-1,4-diene-3,17-dione | thiophenol | tetraiodo-o-benzoquinone | 2', 3'-dihydro-11β-hydroxy-5', 6', 7', 8'-tetraiodo-17-(phenylthio)androsta-1,4-dieno[16α, 17α-b][1,4]benzodioxin-3-one |
| 16 | androsta-1,4-diene-3,11,17-trione | n-butanethiol | tetrachloro-o-benzoquinone | 17-(butylthio)-5', 6', 7', 8'-tetrachloro-2', 3'-dihydro-androsta-1,4-dieno[16α, 17α-b]-[1,4]benzodioxin-3,11-dione |
| 17 | 11β-hydroxyandrost-4-ene-3,17-dione | n-propanethiol | tetrabromo-o-benzoquinone | 5', 6', 7', 8'-tetrabromo-2', 3'-dihydro-11β-hydroxy-17-(propylthio)androst-4-eno[16α, 17α-b]-[1,4]benzodioxin-3-one |
| | 6α, 9-difluoro-11β-hydroxyandrosta-1,4-diene-3,17-dione | thiophenol | tetrabromo-o-benzoquinone | 5', 6', 7', 8'-tetrabromo-6α, 9-difluoro-2', 3'-dihydro-11β-hydroxy-17-(phenylthio)androsta-1,4-dieno[16α, 17α-b][1,4]benzodioxin-3-one |

What is claimed is:

1. A steroid having the formula

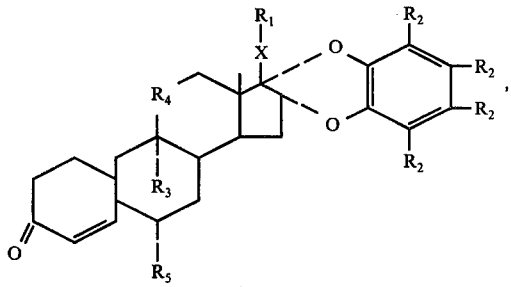

or the 1,2-dehydro derivative thereof, wherein X is
—S—,

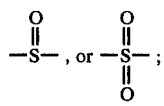

$R_1$ is alkyl, aryl or acyloxyalkyl; $R_2$ is fluoro, chloro, bromo, or iodo; $R_3$ is hydrogen, fluoro, chloro, bromo or iodo; $R_4$ is carbonyl, β-hydroxymethylene or β-acyloxymethylene; and $R_5$ is hydrogen or fluoro; wherein the term "aryl" is phenyl or phenyl substituted with 1 or 2 alkyl, alkoxy, fluoro, chloro, bromo or iodo groups; the terms "alkyl" and "alkoxy" refer to groups having 1 to 10 carbon atoms; and the term "acyloxy" refers to groups of the formula

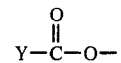

wherein Y is alkyl or aryl.

2. A steroid in accordance with claim 1 wherein X is —S—.

3. A steroid in accordance with claim 1 wherein X is

4. A steroid in accordance with claim 1 wherein X is

5. A steroid in accordance with claim 1 wherein $R_1$ is alkyl.

6. A steroid in accordance with claim 1 wherein $R_1$ is aryl.

7. A steroid in accordance with claim 1 wherein $R_1$ is acyloxyalkyl.

8. A steroid in accordance with claim 1 wherein $R_3$ is fluoro.

9. A steroid in accordance with claim 1 wherein $R_2$ is chloro.

10. A steroid in accordance with claim 1 wherein $R_1$ is alkyl, aryl, or acyloxymethyl; $R_2$ is chloro, $R_3$ is fluoro; $R_4$ is β-hydroxymethylene; and $R_5$ is hydrogen.

11. The steroid in accordance with claim 1, 5',6',7',8'-tetrachloro-9-fluoro-2',3'-dihydro-11β-hydroxy-17-(methylthio)androsta-1,4-dieno[16α,17α-b][1,4]benzodioxin-3-one.

12. The steroid in accordance with claim 1, 5',6',7',8'-tetrachloro-9-fluoro-2',3'-dihydro-11β-hydroxy-17-(methylsulfinyl)androsta-1,4-dieno[16α,17α-b][1,4]benzodioxin-3-one.

13. The steroid in accordance with claim 1, 5',6',7',8'-tetrachloro-9-fluoro-2',3'-dihydro-11β-hydroxy-17-(methylsulfonyl)androsta-1,4-dieno[16α,17α-b][1,4]-benzodioxin-3-one.

14. The steroid in accordance with claim 1, 5',6',7',8'-tetrachloro-17-(ethylthio)-9-fluoro-2',3'-dihydro-11β- hydroxyandrosta-1,4-dieno[16α,17α-b][1,4]benzodioxin-3-one.

15. The steroid in accordance with claim 1, 5',6',7',8'-tetrachloro-17-(ethylsulfinyl)-9-fluoro-2',3'-dihydro-11β-hydroxyandrosta-1,4-dieno[16α,17α-b][1,4]benzodioxin-3-one.

16. The steroid in accordance with claim 1, 5',6',7',8'-tetrachloro-17-(ethylsulfonyl)-9-fluoro-2',3'-dihydro-11β-hydroxyandrosta-1,4-dieno[16α,17α-b][1,4]benzodioxin-3-one.

17. The steroid in accordance with claim 1, 5',6',7',8'-tetrachloro-9-fluoro-2',3'-dihydro-11β-hydroxy-17-(phenylthio)androsta-1,4-dieno[16α,17α-b][1,4]benzodioxin-3-one.

18. The steroid in accordance with claim 1, 5',6',7',8'-tetrachloro-9-fluoro-2',3'-dihydro-11β-hydroxy-17-(phenylsulfinyl)androsta-1,4-dieno[16α,17α-b][1,4]benzodioxin-3-one.

19. The steroid in accordance with claim 1, 5',6',7',8'-tetrachloro-9-fluoro-2',3'-dihydro-11β-hydroxy-17-(phenylsulfonyl)androsta-1,4-dieno[16α,17α-b][1,4]benzodioxin-3-one.

20. The steroid in accordance with claim 1, 17-[[(acetyloxy)methyl]thio]-5',6',7',8'-tetrachloro-9-fluoro-2',3'-dihydro-11β-hydroxyandrosta-1,4-dieno[16α,17α-b][1,4]benzodioxin-3-one.

21. The steroid in accordance with claim 1, 17-[[(acetyloxy)methyl]sulfinyl]-5',6',7',8'-tetrachloro-9-fluoro-2',3'-dihydro-11β-hydroxyandrosta-1,4-dieno[16α,17α-b][1,4]benzodioxin-3-one.

22. The steroid in accordance with claim 1, 17-[[(acetyloxy)methyl]sulfonyl]-5',6',7',8'-tetrachloro-9-fluoro-2',3'-dihydro-11β-hydroxyandrosta-1,4-dieno[16α,17α-b][1,4]benzodioxin-3-one.

* * * * *

UNITED STATES PATENT AND TRADEMARK OFFICE
CERTIFICATE OF CORRECTION

PATENT NO. : 4,094,840
DATED : June 13, 1978
INVENTOR(S) : Ravi K. Varma

It is certified that error appears in the above-identified patent and that said Letters Patent are hereby corrected as shown below:

Column 5, line 40, "C, 63.40;" should read --C, 63.60;--.

Column 6, lines 9 and 10, "[16α1-7α-b]" should read --[16α,17α-b].

Column 10, line 27 "dieno[-" should read "dieno-[--.

Column 13, Example 18, Column 1, the numeral 18 should be inserted before 6α,9-difluoro-11β-.

Column 13, Example 18, Column lll, "difluoro-2',3'-dihydro-11β-" should be deleted and inserted in the second line of Example 18 under Column IV.

Signed and Sealed this

*Twelfth* Day of *December 1978*

[SEAL]

*Attest:*

RUTH C. MASON
*Attesting Officer*

DONALD W. BANNER
*Commissioner of Patents and Trademarks*